(12) United States Patent
Gold et al.

(10) Patent No.: US 11,841,109 B2
(45) Date of Patent: Dec. 12, 2023

(54) MULTI-WORKSTATION COMPUTER DISPLAY SUPPORT STRUCTURE FOR REDUCING EHR-RELATED MEDICAL ERRORS OCCURRING DURING INTER-PROFESSIONAL PATIENT ROUNDS

(71) Applicant: OREGON HEALTH & SCIENCE UNIVERSITY, Portland, OR (US)

(72) Inventors: Jeffrey A Gold, Portland, OR (US); Vishnu Mohan, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 383 days.

(21) Appl. No.: 16/941,132

(22) Filed: Jul. 28, 2020

(65) Prior Publication Data
US 2021/0033243 A1    Feb. 4, 2021

Related U.S. Application Data

(60) Provisional application No. 62/882,366, filed on Aug. 2, 2019.

(51) Int. Cl.
| | |
|---|---|
| *F16M 11/22* | (2006.01) |
| *G16H 40/20* | (2018.01) |
| *G16H 10/60* | (2018.01) |
| *G16H 50/70* | (2018.01) |
| *G16H 70/20* | (2018.01) |

(Continued)

(52) U.S. Cl.
CPC ............ *F16M 11/22* (2013.01); *A61G 12/00* (2013.01); *F16M 11/10* (2013.01); *F16M 11/2021* (2013.01); *G06F 3/1423* (2013.01); *G06Q 10/06316* (2013.01); *G16H 10/60* (2018.01); *G16H 15/00* (2018.01); *G16H 40/20* (2018.01); *G16H 50/20* (2018.01); *G16H 50/70* (2018.01); *G16H 70/20* (2018.01); *A61G 2203/20* (2013.01); *F16M 11/42* (2013.01)

(58) Field of Classification Search
None
See application file for complete search history.

(56) References Cited

U.S. PATENT DOCUMENTS

| | | | | |
|---|---|---|---|---|
| 5,537,127 A | * | 7/1996 | Jingu | F16M 11/24 361/679.04 |
| 5,630,566 A | * | 5/1997 | Case | F16M 11/42 248/122.1 |

(Continued)

*Primary Examiner* — Xanthia C Cunningham
(74) *Attorney, Agent, or Firm* — Stoel Rives LLP (57) ABSTRACT

A method using a specially configured computer display support structure reduces occurrences of medical errors by facilitating real-time, synchronous review of medical data by rounding professionals during patient rounds. The support structure includes an upright column assembly that has a column assembly base and six sides. Mounting brackets fixed to non-contiguous sides of the column assembly receive back plates of a system device mounting assembly, each of which includes a pivot arm that receives a system device arm. The system device arm is pivotable at opposing ends and terminates in a coupling member at its distal end. The coupling member is connected to a video display that has an angularly positionable display screen. In some embodiments, a keyboard tray, on which a keyboard and computer mouse rest, is connected to the coupling member.

8 Claims, 9 Drawing Sheets

(51) Int. Cl.
*G16H 50/20* (2018.01)
*G16H 15/00* (2018.01)
*F16M 11/10* (2006.01)
*F16M 11/20* (2006.01)
*G06F 3/14* (2006.01)
*A61G 12/00* (2006.01)
*G06Q 10/0631* (2023.01)
*F16M 11/42* (2006.01)

(56) References Cited

U.S. PATENT DOCUMENTS

| | | | | |
|---|---|---|---|---|
| 6,012,591 A * | 1/2000 | Brandenberg | ............ | A47F 5/04 |
| | | | | 211/26 |
| 6,449,143 B2 * | 9/2002 | Rooyakkers | ......... | A47B 83/001 |
| | | | | 361/679.04 |
| 7,134,719 B2 * | 11/2006 | Moglin | .................... | A47C 7/72 |
| | | | | 297/188.21 |
| 7,246,780 B2 * | 7/2007 | Oddsen, Jr. | ............ | F16M 13/02 |
| | | | | 248/125.7 |
| 8,102,333 B2 * | 1/2012 | Kondo | .................. | G06F 3/1446 |
| | | | | 345/905 |
| 8,191,487 B2 * | 6/2012 | Theesfeld | ............... | F16M 11/24 |
| | | | | 108/50.01 |
| 8,462,103 B1 * | 6/2013 | Moscovitch | ........... | F16M 13/02 |
| | | | | 345/55 |
| 8,905,496 B2 * | 12/2014 | Burgess | ................. | A47B 21/00 |
| | | | | 108/50.02 |
| 9,228,693 B2 * | 1/2016 | Ditges | .................... | F16M 11/24 |
| 9,247,861 B2 * | 2/2016 | Kan | ...................... | H04N 5/655 |
| 9,585,470 B2 * | 3/2017 | Mattar | .................... | A47B 51/00 |
| 9,642,477 B2 * | 5/2017 | Kontschak | ................. | G06F 1/16 |
| 9,980,561 B1 * | 5/2018 | Constantino | ........... | A47B 21/02 |
| 10,376,042 B1 * | 8/2019 | Johnson | ................ | F16M 11/06 |
| 2007/0176060 A1 * | 8/2007 | White | .................... | A61B 50/10 |
| | | | | 248/124.1 |
| 2012/0248263 A1 * | 10/2012 | Grotenhuis | ............ | A47B 21/02 |
| | | | | 248/123.2 |
| 2013/0341476 A1 * | 12/2013 | Hazzard | ................ | A47B 21/0314 |
| | | | | 248/231.71 |
| 2014/0070059 A1 * | 3/2014 | Vieira | .................... | A47B 97/00 |
| | | | | 248/122.1 |
| 2016/0119593 A1 * | 4/2016 | Schultz | ................ | H04N 5/2251 |
| | | | | 348/77 |

* cited by examiner

Rounding Checklist

| 1. Vitals | ✓ |
|---|---|
| Blood pressure | 266 |
| Heart rate | 266 |
| Body temperature | 266 |
| Respiratory rate | 266 |
| Pulse-oximetry | 266 |

| 2. Ventilator | ✓ |
|---|---|
| Time of intubation | 266 |
| Mode of mechanical ventilation | 266 |
| Initial ventilator settings | 266 |
| Changes to ventilator settings | 266 |
| Duration of mechanical ventilation | 266 |
| Blood gas | 266 |

| 3. Laboratory results | ✓ |
|---|---|
| pH | 266 |
| $K^+$ | 266 |
| Bilirubin | 266 |
| Lactate | 266 |
| Blood culture | 266 |
| Platelets | 266 |
| PT/INR | 266 |

| 4. Imaging | ✓ |
|---|---|
| Report | 266 |
| MRI | 266 |
| CT | 266 |
| Ultrasound | 266 |

| 5. Nursing | ✓ |
|---|---|
| Cognition | 266 |
| Daily activities | 266 |
| Caregiver support | 266 |
| Home environment | 266 |
| Health history | 266 |
| Symptom status | 266 |
| Medication issues | 266 |
| Wounds | 266 |
| Incisions | 266 |
| Emotional status | 266 |
| Pain scores | 266 |

| 6. Pharmacy | ✓ |
|---|---|
| Medical history | 266 |
| Allergies | 266 |
| Contraindications | 266 |
| Current medications | 266 |
| Renal & hepatic dosing | 266 |
| Patient-specific factors | 266 |
| Therapeutic equivalents | 266 |

MULTI-WORKSTATION COMPUTER DISPLAY SUPPORT STRUCTURE FOR REDUCING EHR-RELATED MEDICAL ERRORS OCCURRING DURING INTER-PROFESSIONAL PATIENT ROUNDS

FEDERALLY SPONSORED RESEARCH OR DEVELOPMENT

This invention was made with government support under Grant Number AHRQ R01 HS23793 awarded by the Agency for Healthcare Research and Quality. The government has certain rights in the invention.

COPYRIGHT NOTICE

© 2020 OREGON HEALTH & SCIENCE UNIVERSITY. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This disclosure relates to electronic health records-related medical errors and, in particular, a multi-workstation computer display support structure for reducing electronic health records-related medical errors occurring during inter-professional patient rounds.

BACKGROUND INFORMATION

There has been a dramatic rise in the adoption of Electronic Health Records ("EHRs") over the past decade. While it has been felt that EHRs could dramatically reduce medical errors, a number of studies suggest that EHRs are responsible for a new class of medical errors ("EHR-related medical errors"). The root causes of these errors fall into many categories including data fragmentation, over-completeness (including excessive redundancy and "cut-and-paste"), data recognition errors, and perhaps most importantly, cognitive errors. Thus, the etiology of these EHR-related medical errors is multifactorial. And the Intensive Care Unit ("ICU") environment is particularly susceptible because ICU-specific factors such as the severity of illness exhibited by the patients, the large volume of medical data points generated during patient care, and the professional diversity of members of the care team significantly increase the risk of an EHR-related medical error occurring.

These factors all converge during patient rounds. For patients in the ICU, current best practice mandates daily inter-professional patient rounds ("IP patient rounds"), where the physician, bedside nurse, pharmacists and other professionals are each responsible for extracting data from the EHR that is verbalized on IP patient rounds and used for clinical decision making. The integrity and veracity of these data are essential for effective clinical decision making. Studies suggest that access to necessary data is a major barrier to effective IP patient rounds. Complicating the issue are studies demonstrating that each member of the IP patient rounding team appears to use the EHR differently and has varying opinions on the quality and veracity of the data within the system.

Historically, clinicians have sought to reduce the incidence of EHR-related medical errors through the use of rounding tools. Rounding tools are paper or computer-based documentation tools such as checklists, workflow diagrams, or standardized forms designed to reduce EHR-related medical errors by including case-relevant medical data on the rounding tool, preventing information loss due to inter-professional, verbal communication and providing evidence-based, standard-of-care guidance to health care providers making decisions about a patient's care. However, many rounding tools are developed locally, often by a single institution, department, care-team, or even a single individual, leading to significant variability among rounding tools. The wide variability in the rounding tools employed creates further risk of EHR-related medical errors when patient care requires inter-departmental or inter-professional communication among teams using different rounding tools. Thus, standardization of rounding tools is a first step towards reducing EHR-related medical errors.

The alarming rate of EHR-related medical errors may be mitigated not only by standardization of rounding tools, but also by ensuring the presence of case-relevant medical data on the rounding tool to increase the likelihood of correctly communicating case-relevant medical data and emphasizing continuous monitoring and improvement of the EHR itself with a focus on four dimensions: clinical content, the human/computer interface, people, and workflow/communication.

Especially relevant for the ICU setting is the sheer amount of data generated during routine patient care. Successful use of an EHR is dependent upon providers being able to efficiently navigate and integrate these data points and trends. Further, the high degree of acuity of the average ICU patient often results in the need to make a large number of decisions in a short timeframe juxtaposed with the need to rapidly process a large influx of information, often in real-time. Consequently, it is easy to envision how data fragmentation and poor user-interfaces can lead to significant issues with clinical cognition, leading to medical errors.

The inter-professional nature of ICU care creates its own issues. In studies conducted in diverse clinical settings, poor communication among members of an ICU care team has been shown to be a major source of medical errors, leading to both morbidity and mortality. These medical errors are frequently driven by a number of cognitive biases that influence clinical decision making. Examples include anchoring bias, framing effects, and diagnostic momentum. Many cognitive biases are influenced by what medical data are or are not available to the clinician (availability bias), or whether the medical data are visualized at an appropriate time during decision making. Thus, issues with the availability and visualization of the medical data place the EHR at the *nexus* of the problem.

SUMMARY OF THE DISCLOSURE

The disclosed multi-workstation computer display support structure and methods are useful for reducing EHR-related medical errors that occur during inter-professional patient rounds. Some of the disclosed embodiments use a multi-workstation computer display support structure that is placeable at a patient's bedside and configured to provide a central location for real-time, synchronous viewing of the patient's medical data and any modifications made thereof throughout the rounding process by the rounding professionals.

A preferred multi-workstation computer display support structure is used in concert with a method for reducing EHR-related medical errors from occurring during interprofessional patient rounds. The computer display support structure includes an upright column assembly that has a column assembly base. The upright column assembly defines a longitudinal axis that has an exterior surface and a periphery. Multiple mounting brackets are positioned at different spaced-apart locations on the exterior surface and around the periphery of the upright column assembly. Multiple system device mounting assemblies are configured to be attached to the multiple mounting brackets so that different pairs of the multiple system device mounting assemblies, when attached to an associated one of the multiple mounting brackets, are spaced apart from each other in a direction generally along the longitudinal axis of the upright column assembly and are configured for pivotal movement independent of each other. A video display is mounted to each one of the different pairs of the multiple system device mounting assemblies and has a display screen that provides for an observer a viewing angle that is adjustable in correspondence with the pivotable movement. A video display source controller capable of responding to a user-provided command is used to select a source of video for delivery to one or more of the video displays.

Additional aspects and advantages will be apparent from the following detailed description of preferred embodiments, which proceeds with reference to the accompanying drawings.

DETAILED DESCRIPTION OF PREFERRED EMBODIMENTS

The following is a set of definitions of terms used in the detailed description of several example scenarios of IP rounds carried out in accordance with the disclosed computer display support structure and method of using it.

"Clinical Decision Rules" (or "CDR") are evidence-based algorithms derived from original research to provide guidance for clinical decision making. CDRs can be "directive" if they suggest a course of action or "assistive" if they provide evidence to enhance clinical judgment.

"Electronic Health Record" (or "EHR") is a digital version of a patient-centered record including patient medical histories, diagnoses, medications, treatment plans, immunization dates, allergies, radiology images, and laboratory test results.

"Electronic Health Record System" (or "EHR System") is a computer-based, real-time electronic health record management system that allows for secure access and modification to an EHR by an authorized user from more than one health organization such as laboratories, specialists, medical imaging facilities, pharmacies, emergency facilities, and school and workplace clinics. EHR Systems offer access to customizable, evidence-based tools that health care providers can use to make decisions about a patient's care including customizable flowsheets, tracking and trending case-relevant medical data over time, identifying when patients are due for a preventative screening or checkup, or identifying patients with high-risk circumstances.

"Flowsheet" is a customizable graphic representation, in outline or picture format, of a standardized clinical intervention process that displays multiple data fields and prompts the user take temporally relevant action(s) to complete the intervention including responding to any CDR prompts (either directive or assistive), reviewing and editing data fields, reviewing and editing data fields from previous interventions, flagging the patient's high-risk circumstances, prompting the user to provide missing case-relevant medical data, and entering additional chart notes in a patient record.

"Workflow engine" is a set of logic-based rules held as a template file in the EHR System that defines what activities are available to an EHR System user based on a specified clinical context. EHR System activities include data retrieval, chart review, database lookups, preference lists, navigators, snapshot and summary reports, flowsheets, related orders, and encounter signing.

FIGS. 1-5 show in several orientations a computer display support structure 10 that is configured in a preferred embodiment as a three-workstation computer display support structure for reducing EHR-related medical errors during IP patient rounds. Computer display support structure 10 includes an upright column assembly 12 of hexagonal shape and length that defines a longitudinal axis 14. Three tubular legs 16$_1$, 16$_2$, and 16$_3$, mutually angularly spaced apart by 120°, extend radially from a bottom end of upright column assembly 12 to form a column assembly base 18 for computer display support structure 10. (Similar components and features identified by a common reference numeral followed by different subscripts are sometimes referred to collectively by only the reference numeral.) A caster wheel 20 mounted at the free end of each leg 16 provides translational and rotational mobility to computer display support structure 10. The exterior surface of upright column assembly 12 is formed of six sides $22_1$, $22_2$, $22_3$, $22_4$, $22_5$, and $22_6$, of which non-contiguous sides $22_1$, $22_3$, and $22_5$ incorporate respective mounting brackets $24_1$, $24_3$, and $24_5$. Mounting brackets 24 are fixed to sides 22 from which tubular legs 16 do not extend to provide working space for users of computer display support structure 10. Mounting brackets 24 are guide rails that extend along the length of upright column assembly 12, and each of mounting brackets 24 receives a back plate 40 of a system device mounting assembly 42 that is slideable along the length of its associated mounting bracket 24 and is securable in place by a clamp (not shown). Each system device mounting assembly 42 includes a generally L-shaped pivot arm 46, with its leg extending horizontally from back plate 40 and its ascender oriented vertically. The ascender has a free end that is configured to receive, and form a pivot joint 48 with, a system device arm 50. System device arm 50 is pivotable at two opposite ends and supports one of a number of suitable system devices.

In the embodiment shown, each of mounting brackets $24_1$, $24_3$, and $24_5$ receives three system device mounting assemblies $42_1$, $42_2$, and $42_3$ and a CPU platform 54 that are positioned at consecutive descending heights along longitudinal axis 14.

Figure 4:
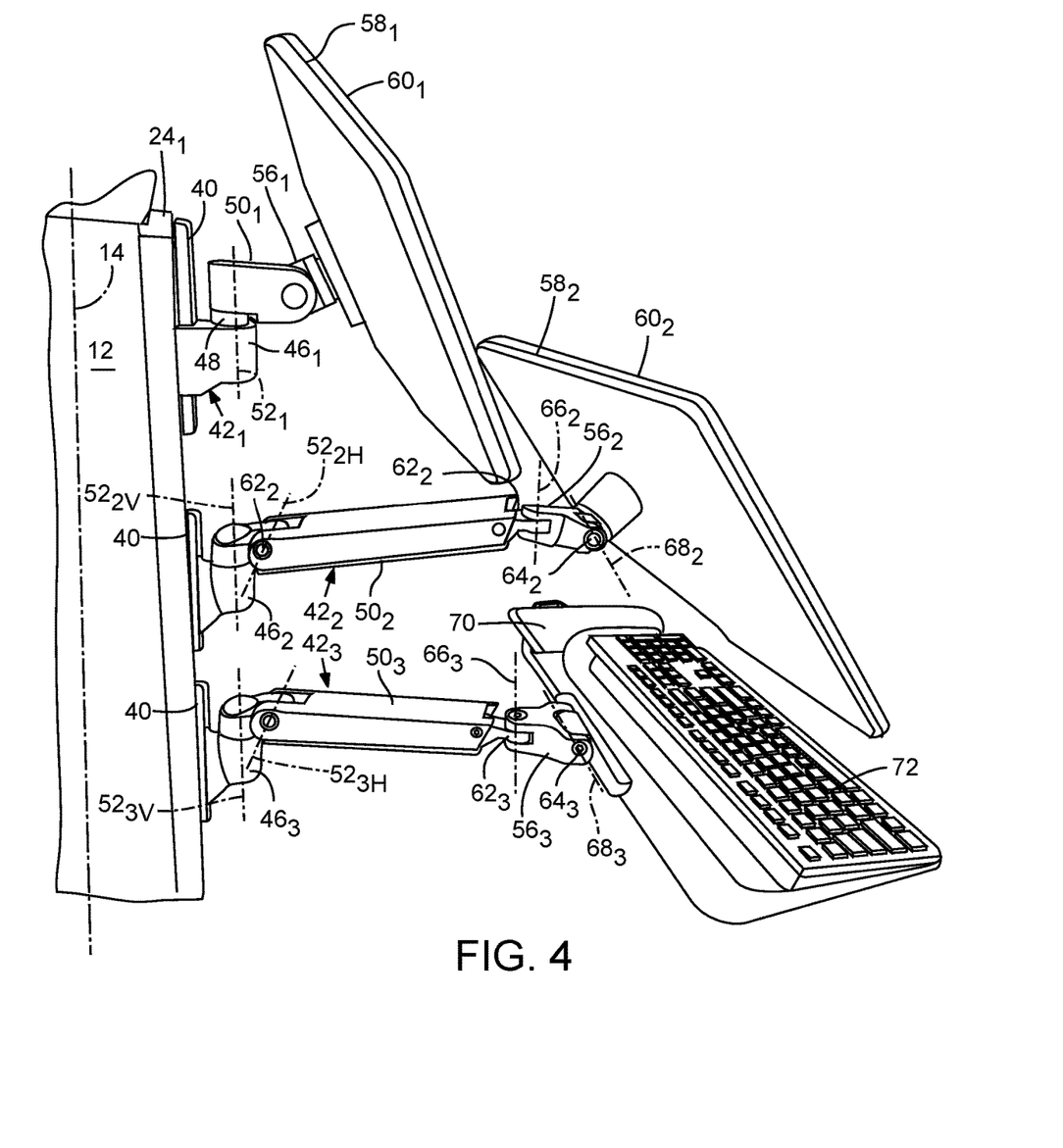
FIG. 4 is an enlarged fragmentary side elevation view of three system device mounting assemblies configured to support two video displays and a keyboard tray at one of the workstations of the computer display support structure of FIG. 1.

System device mounting assembly $42_1$ includes a pivot arm $46_1$ that is pivotally coupled to a shorter-length system device arm $50_1$. System device arm $50_1$ terminates in a coupling member $56_1$, which is a ball and socket assembly, that is connected to a back side of a video display $58_1$ having a display screen $60_1$. Coupling member $56_1$ allows angular positioning of display screen $60_1$ in three-dimensional space.

System device mounting assembly $42_2$ includes a pivot arm $46_2$ that is pivotally connected to a longer length system device arm $50_2$. The pivotal connection to pivot arm $46_2$ enables pivotal movement about an axis $52_{2v}$, which is parallel to longitudinal axis 14, and pivotal movement about an axis $52_{2h}$, which is transverse to longitudinal axis 14 and axis $52_{2v}$. System device arm $50_2$ terminates in a coupling member $56_2$, which at its proximal end forms a pivot joint $62_2$ with system device arm $50_2$ and at its distal end forms a pivot joint $64_2$ with a back side of a video display $58_2$ having a display screen $60_2$. Pivot joint $62_2$ provides pivotal movement of video display $58_2$ about an axis $66_2$ that is parallel to longitudinal axis 14, and pivot joint $64_2$ provides pivotal movement of video display $58_2$ about an axis $68_2$ that is transverse to longitudinal axis 14 and axis $66_2$. Pivot joints $62_2$ and $64_2$ cooperate to allow translation of display screen $60_2$ in a horizontal plane and tilt relative to a vertical plane.

System device mounting assembly $42_3$ includes a pivot arm $46_3$ that is pivotally connected to a longer length system device arm $50_3$. The pivotal connection to pivot arm $46_3$ enables pivotal movement about an axis $52_{3v}$, which is parallel to longitudinal axis 14, and pivotal movement about an axis $52_{3h}$, which is transverse to longitudinal axis 14 and axis $52_{3v}$. System device arm $50_3$ terminates in a coupling member $56_3$, which at its proximal end forms a pivot joint $62_3$ with system device arm $50_3$ and at its distal end forms a pivot joint $64_3$ with a back side of a keyboard tray 70 on which a keyboard 72 and a computer mouse 74 rest. Pivot joint $62_3$ provides pivotal movement of keyboard tray 70 about an axis $66_3$ that is parallel to longitudinal axis 14, and pivot joint $64_3$ provides pivotal movement of keyboard tray 70 about an axis $68_3$ that is transverse to longitudinal axis 14 and axis $66_3$. Pivot joints $62_3$ and $64_3$ cooperate to allow translation of keyboard tray 70 in a horizontal plane and tilt relative to a vertical plane.

Figure 1:
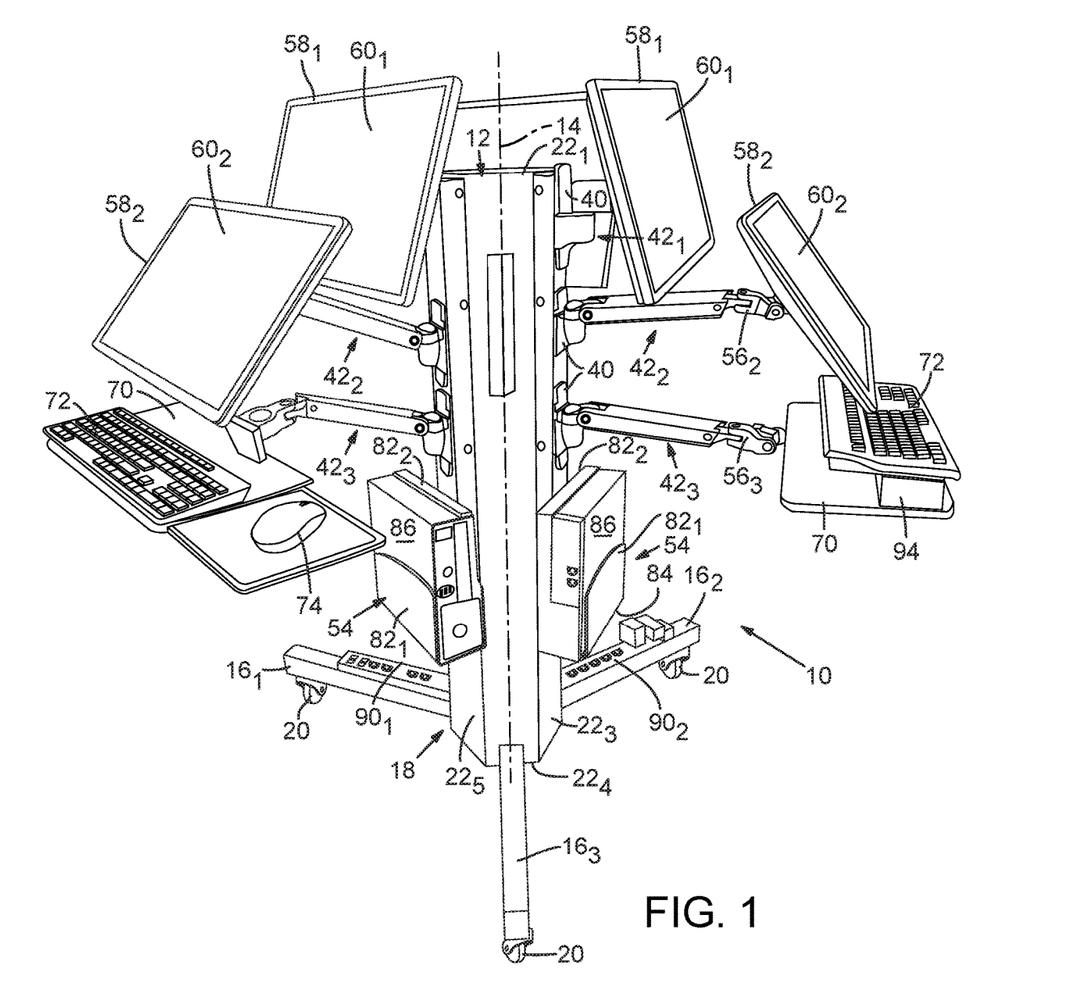
FIG. 1 is a perspective view of the disclosed computer display support structure in an embodiment that is configured with three workstations.
Figure 2:
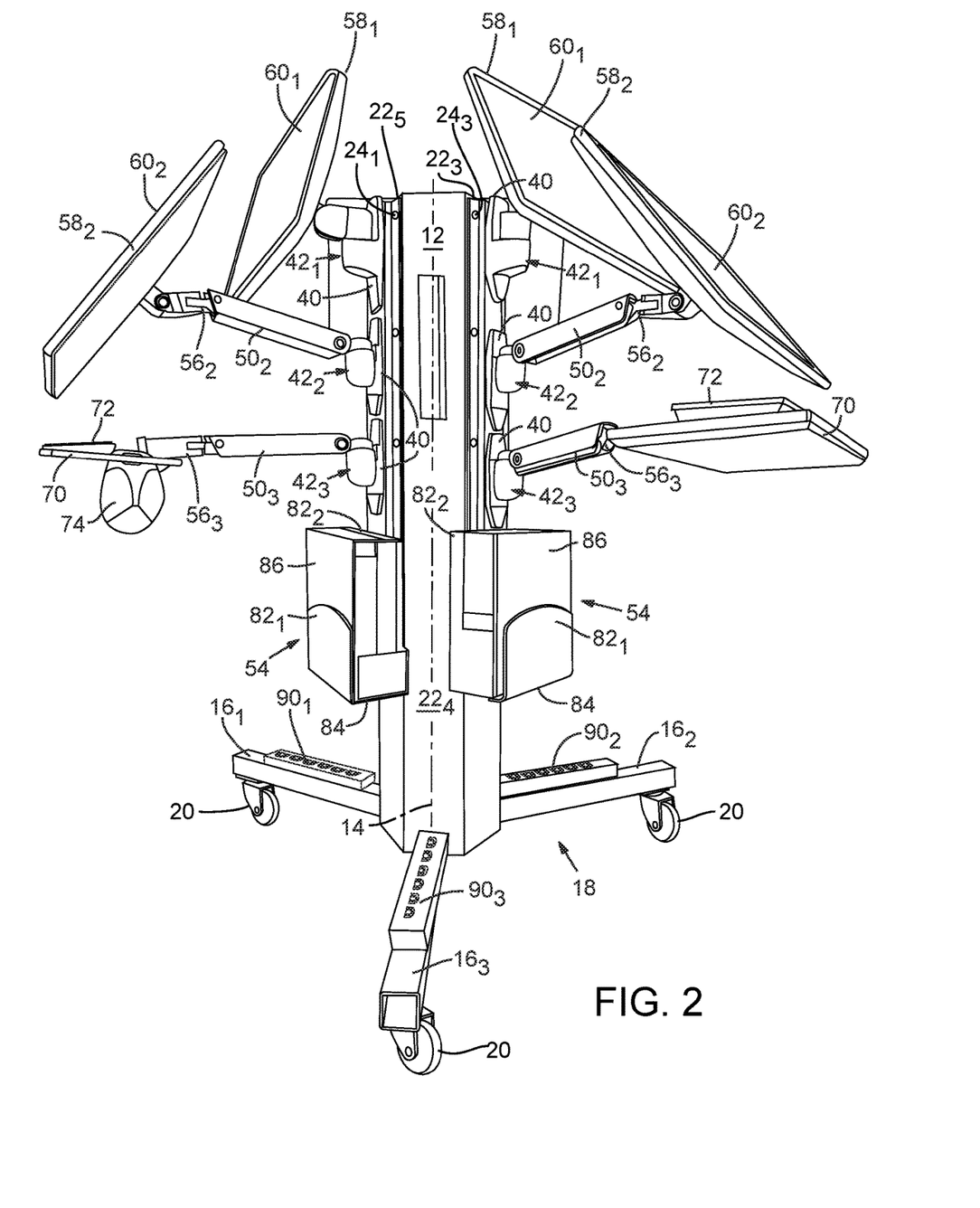
FIG. 2 is a perspective view showing the column assembly of and electronic equipment associated with the computer display support structure of FIG. 1.
Figure 3:
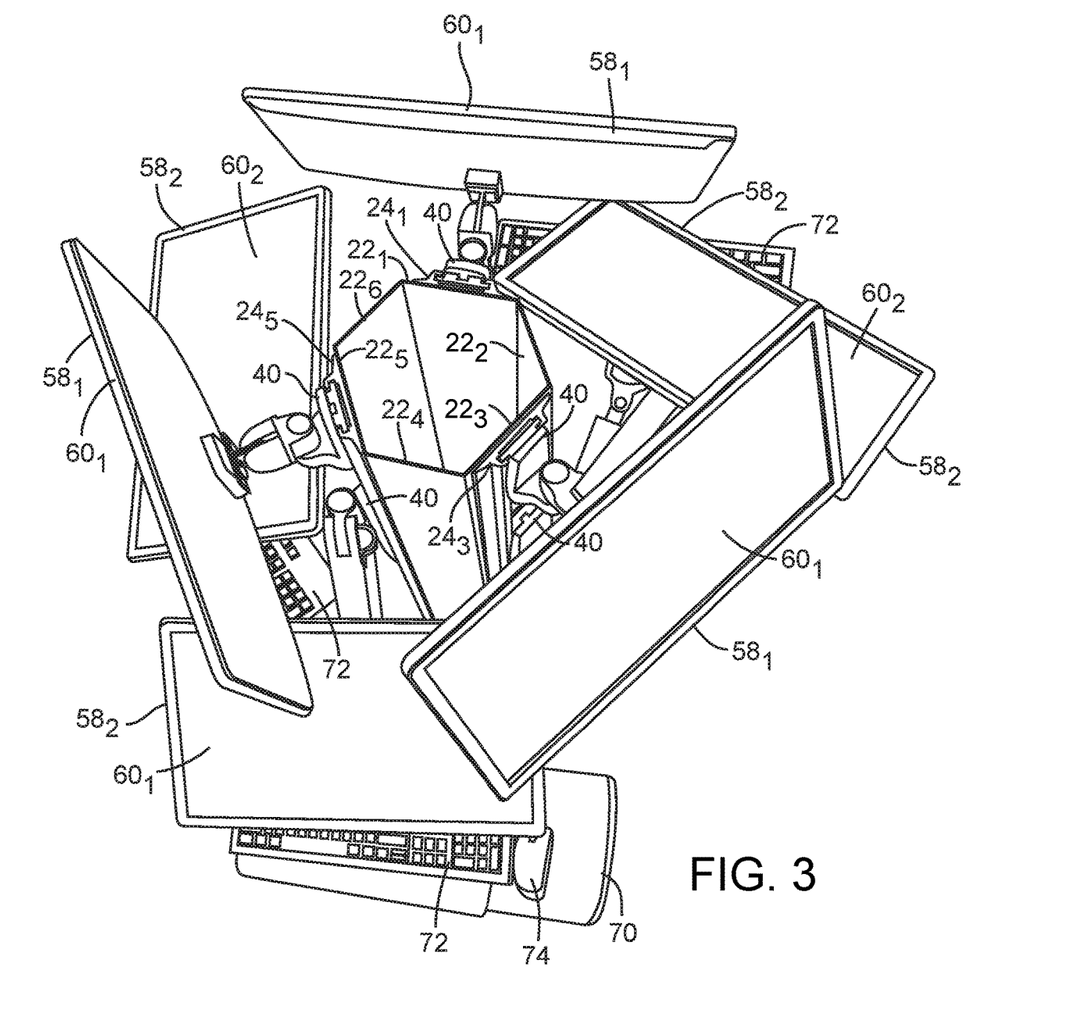
FIG. 3 is an oblique top view of the computer display support structure of FIG. 1.

CPU platform 54 is a U-shaped bracket that includes two channel walls $82_1$ and $82_2$ and a support surface 84 on which a CPU 86 rests between walls $82_1$ and $82_2$. The proximal and distal sides of support surface 84 are fixed at right angles to the bottom edges of channel walls $82_1$ and $82_2$, respectively, with walls $82_1$ and $82_2$ aligned in parallel to form a U-shape.

In the embodiment shown, one or more straps (not shown) secure CPU power supplies $90_1$, $90_2$, and $90_3$ to the superior aspect of legs $16_1$, $16_2$, and $16_3$, respectively. Each of the securing straps encircles both a CPU power supply 90 and its supporting tubular leg 16 in a direction transverse to its length.

In the embodiment shown, one of the three keyboard trays 70 supports a video display source controller 94 on which one of the keyboards 72 and computer mice 74 rest.

In an alternative embodiment, exterior surface 22 of upright column assembly 12 is polygonal, with more or fewer than six sides. In another alternative embodiment, exterior surface 22 of upright column assembly 12 is circular or elliptical.

In an alternative embodiment, a suitable column assembly base 18 stabilizes the upright column assembly 12 vertically while remaining capable of passing through narrow corridors and doorways by reducing the width of column assembly base 18 to be less than the widths of corridors or doorways. In another alternative embodiment, there are no caster wheels 20 attached to upright column assembly base 18. In further alternative embodiments, column assembly base 18 may be a set of multiple radially extending segments of unsegmented legs, forming a contiguous, flanged-out pedestal. In still further alternative embodiments, the center of mass of upright column assembly 12 is lowered by the addition of mass to column assembly base 18 in order to further stabilize upright column assembly 12 vertically.

In some alternative embodiments, mounting brackets 24 are quadrilaterally shaped and are selectively located on exterior surface 22 of upright column assembly 12. In other alternative embodiments, mounting brackets 24 are sized to receive a single back plate 40 of a system device mounting assembly 42. In further alternative embodiments, mounting brackets 24 receive back plate 40 that is securable to exterior surface 22 of upright column assembly 12 by one or more fasteners, the fasteners including a set of bolts, screws, rivets, or nails. In still further alternative embodiments, mounting brackets 24 receive a back plate 40 that is securable to exterior surface 22 of upright column assembly 12 by an adhesive or a set of welds.

In some embodiments, system device mounting assembly 42 is secured directly to exterior surface 22 of upright column assembly 12 by one or more fasteners, the fasteners including a set of bolts, screws, rivets, or nails. In other alternative embodiments, system device mounting assembly 42 is secured directly to exterior surface 22 of upright column assembly 12 by an adhesive or a set of welds.

Figure 5:
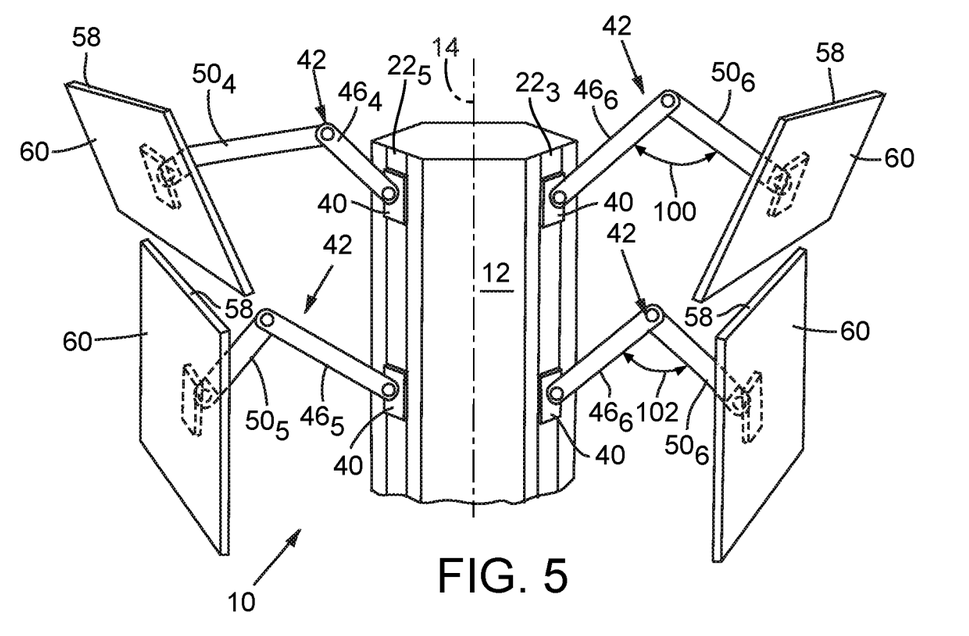
FIG. 5 is a diagram showing, at each of two adjacent workstations of the computer display support structure of FIG. 1, upper and lower video displays positioned at different distances laterally from the upright support column through various configurations by articulation of the system device mounting assemblies.

FIG. 5 is a simplified diagram showing a suitable configuration of computer display support structure 10 that places video displays 58 at different distances laterally from upright column assembly 12. In the left-side embodiment shown, video displays 58 are placed at different distances laterally from upright column assembly 12 because one or more of pivot arms $46_4$ and $46_5$ and system device arms $50_4$ and $50_5$ are of different lengths. In the right-side embodiment shown, pivot arms $46_6$ and system device arms $50_6$ are of the same lengths and video displays 58 are placed at different distances laterally from upright column assembly 12 by adjusting angles of articulation 100 and 102 between pivot arms $46_6$ and system device arms $50_6$.

In some embodiments, CPU power supply 90 can receive power from an external source. In other embodiments, CPU platform 54 can be operatively attached to either video display 58 or system device mounting assembly 42.

Computer display support structure 10 is configured to reduce the incidence of medical errors occurring during patient rounds by facilitating communication during IP patient rounds. Specifically, a method 200 practiced using computer display support structure 10 reduces the risk of a rounding professional engaging in several cognitive biases by disseminating medically appropriate, temporally relevant, non-fragmented, and patient-specific medical data that are simultaneously viewable from a central location in real-time by several, typically three or more, rounding professionals.

Figure 6:
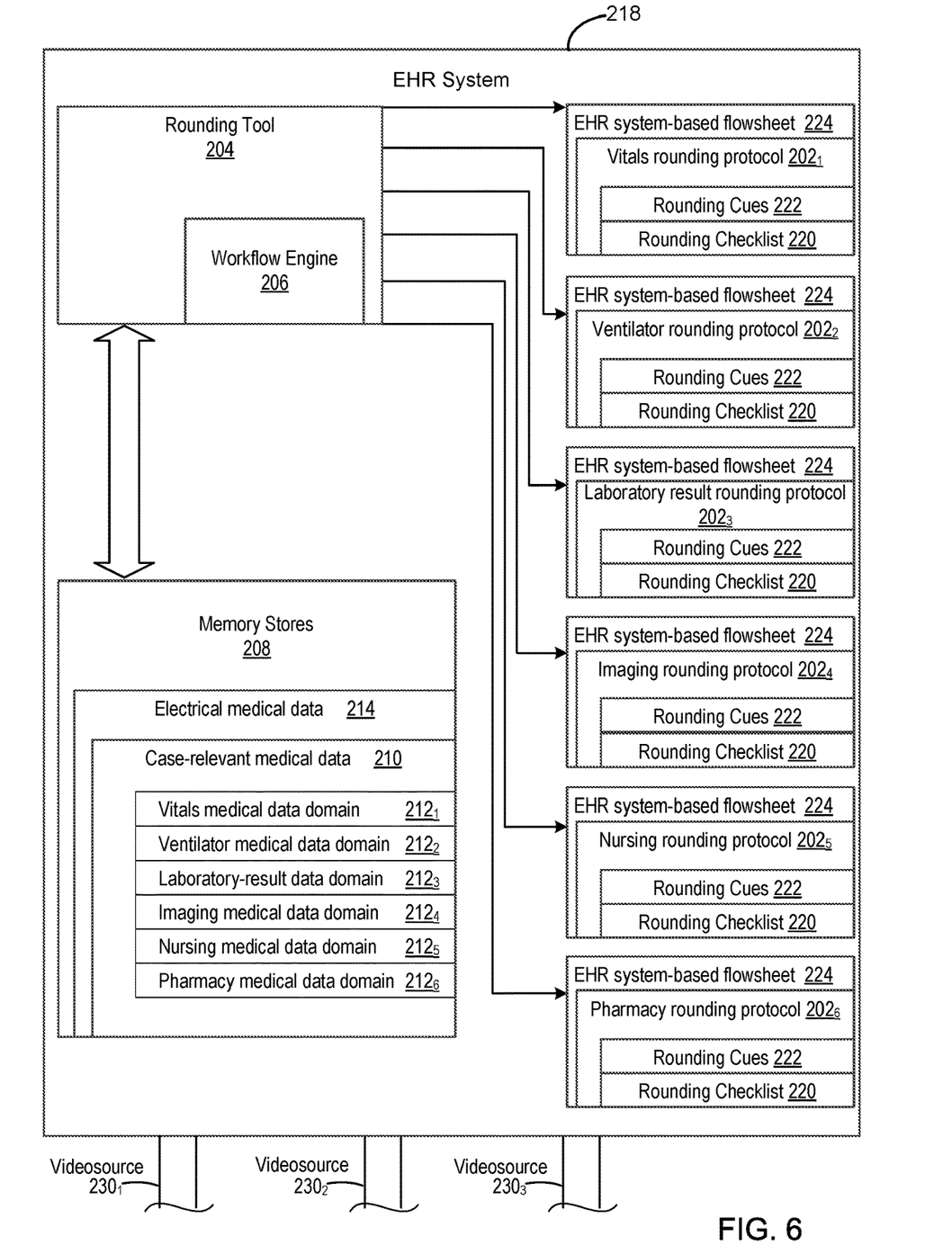
FIG. 6 is a hybrid block diagram and process flow diagram showing the steps performed using components of the computer display support structure of FIG. 1 in generating a rounding protocol for graphical display according to the disclosed method.

FIG. 6 is a hybrid block diagram and process flow diagram showing the steps performed in generating a set of rounding protocols 202 for graphical display according to method 200. A rounding tool 204 executes a workflow engine 206 to retrieve from memory stores 208 case-relevant medical data 210 from a set of case-relevant medical data domains 212 from the entirety of electronic medical data 214 of a single patient. Suitable memory stores 208 are preferably integrated into an electronic health record (EHR) system 218 running on a networked server computer from which case-relevant medical data 210 can be retrieved remotely. A suitable rounding protocol 202 contains a set of pre-determined instructions that delineate the steps of the rounding protocol and prescribes parameters for one or more rounding cues and one or more rounding checklists. A suitable rounding checklist 220 preferentially includes a medical consensus, standard-of-care list of patient-specific actions to be completed by the medical rounding professionals prior to terminating the patient rounds. In some embodiments, rounding checklist 220 includes a customized list of patient-specific actions to be completed by the medical rounding professionals prior to terminating the patient rounds. A suitable rounding cue 222 is a temporally relevant, graphically displayed signal, generated by a rounding protocol 202 according to CDR-based criteria that prompt rounding professionals 240 to take action. In another embodiment, suitable rounding cue 222 is a temporally relevant auditory signal.

Rounding tool 204 assimilates case-relevant medical data 210 retrieved from case-relevant medical data domains 212 into the set of rounding protocols 202 and generates a set of rounding protocols 202, rounding checklists 220, and rounding cues 222. A suitable set of rounding protocols 202, rounding checklists 220, and rounding cues 222 is preferably set forth in an EHR System-based flowsheet 224. EHR System 218 disseminates rounding protocol 202 graphically through a networked video source 230 to display on a display screen 60 that is supported by computer display support structure 10.

In some embodiments, rounding protocols 202 adhere to CDR-based standards-of-care for IP patient rounding. In other embodiments, rounding protocols 202 adhere to customized standards for IP patient rounding. In further embodiments, rounding protocols 202 are executed independently from EHR System 218.

In some embodiments, rounding tool 204 generates a profession-specific presentation schedule that prescribes a sequence for each rounding professional to participate in the patient rounds, based on each rounding professional's scope of practice. In some embodiments, the profession-specific presentation schedule prescribes that the sequence be: (1) a physician or a rounding professional with an equivalent scope-of-practice to that of the physician, (2) a nurse or a rounding professional with an equivalent scope-of-practice to that of the nurse, and (3) a pharmacist or a rounding professional with an equivalent scope-of-practice to that of the pharmacist.

With reference to FIG. 6, in some embodiments, the case-relevant medical data domains include a vitals medical data domain $212_1$, a ventilator medical data domain $212_2$, a laboratory-result medical data domain $212_3$, an imaging medical data domain $212_4$, a nursing medical data domain $212_5$, and a pharmacy medical data domain $212_6$. In some embodiments, vitals medical data domain $212_1$ includes a blood pressure data field, a heart rate data field, a body temperature data field, a respiratory rate data field, and a pulse oximetry data field. In some embodiments, vitals medical data domain $212_1$ includes trended, historical vitals data taken from the patient within seventy-two hours prior to the patient rounds. In some embodiments, ventilator medical data domain $212_2$ includes a time-of-intubation data field, a mode-of-mechanical-ventilation data field, an initial-ventilator-settings data field, a changes-to-ventilator-settings data field, a duration-of-mechanical-ventilation data field, and a blood-gas data field. In some embodiments, laboratory-result medical data domain $212_3$ includes a pH data field, a K+ data field, a Bilirubin data field, a lactate data field, a blood cultures data field, a platelets data field, and a PT/INR data field. In some embodiments, imaging medical data domain $212_4$ incudes a report data field, a MRI data field, a CT data field, and an ultrasound data field. In further embodiments, imaging medical data domain $212_4$ includes one or more source images. In some embodiments, nursing medical data domain $212_5$ includes a cognition data field, a daily-activities data field, a caregiver-support data field, a home-environment data field, a health-history data field, a symptom-status data field, a medication-issues data field, a wounds data field, an incisions data field, an emotional status data field, and a pain-scores data field. In some embodiments, pharmacy medical data domain $212_6$ includes a medical history data field, an allergies data field, a contraindications data field, a current-medications data field, a renal-and-hepatic-dosing data field, a patient-specific-factors data field, and a therapeutic-equivalents data field.

Figures 7A, 7B:
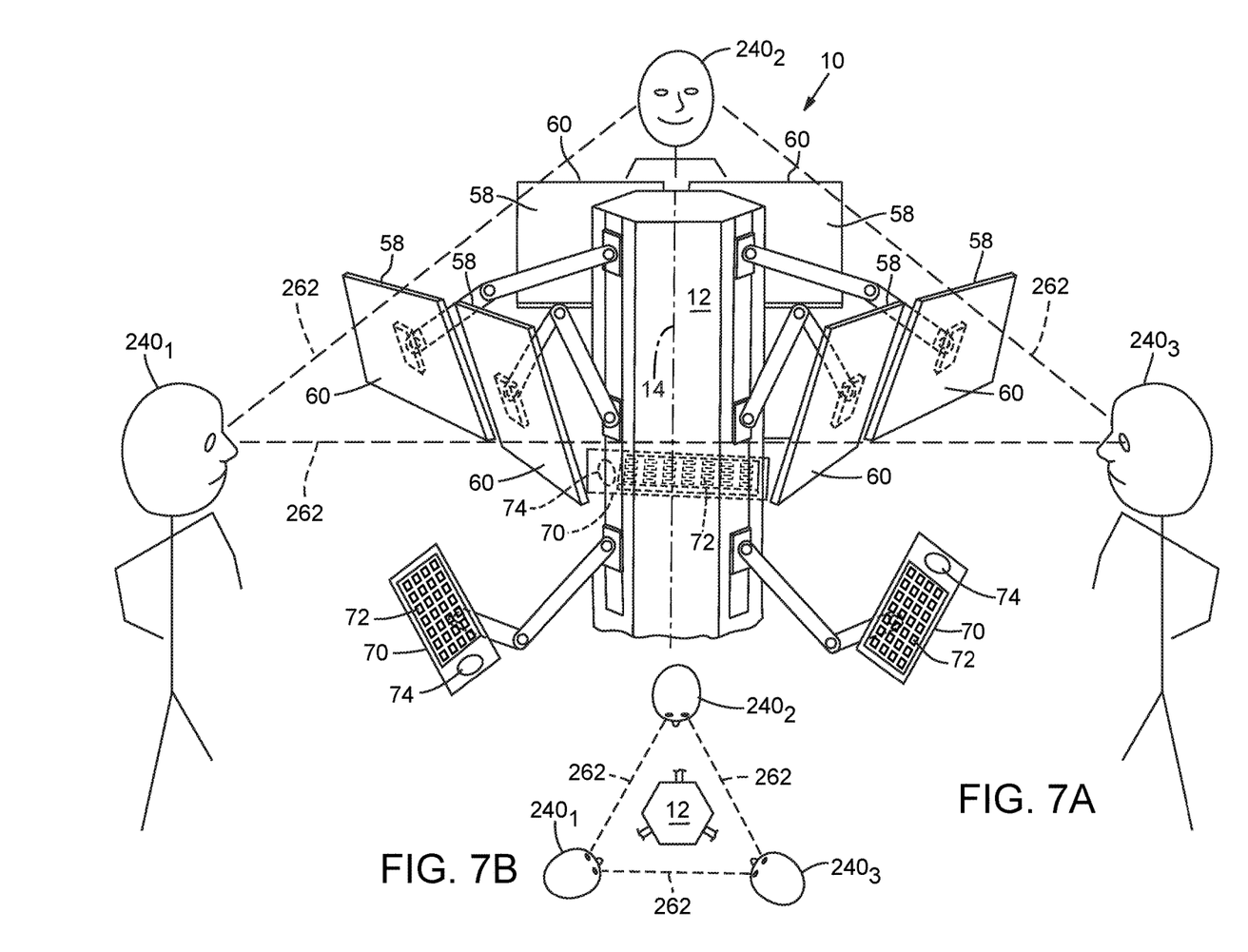
FIGS. 7A and 7B are diagrams showing respective fragmentary side and top plan views of the video displays independently positioned to locations in space that avoid obstructing eye-contact sightlines between adjacent ones of a rounding leader, an order-entry rounding professional, and a scheduled presenting rounding professional using the computer display support structure of FIG. 1.

FIGS. 7A and 7B are diagrams showing video displays 58 independently positioned to locations in space that avoid obstructing eye-contact sightlines 262 between different pairs of rounding leader $241_1$, order-entry rounding professional $240_2$, and scheduled presenting rounding professional $240_3$. Video displays 58 preferably are suitably positioned so that each of video displays 58 is set below each sightline 262. Rounding leader $240_1$, order-entry rounding professional $240_2$, and scheduled presenting rounding professional $240_3$ periodically make eye contact while facing upright column assembly 12 in order to enhance communication during IP Patient Rounds.

Figure 8:
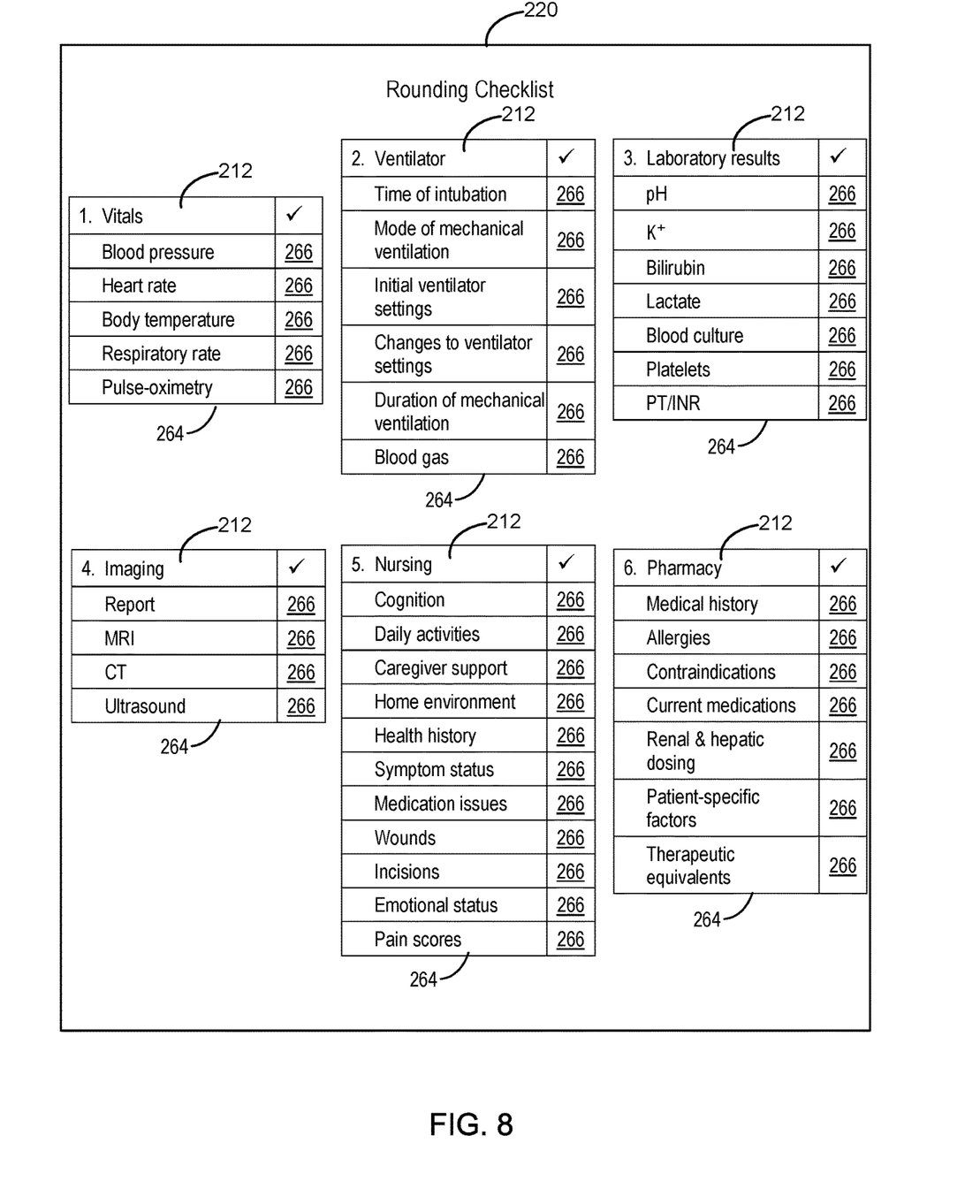
FIG. 8 is an exemplary representation of a rounding checklist setting forth data fields that are organized by case-relevant medical data domains and evaluated by medical professionals.

FIG. 8 is an exemplary representation of a rounding checklist 220 setting forth data fields that are organized by case-relevant medical data domains 212 and evaluated by the medical professionals. Each case-relevant medical data domain 212 has a set of checklist fields 264 whose nomenclature is analogous to the respective nomenclature of the data fields of each case-relevant medical data domain 212. Checklist fields 264 each have an empty check-box 266 that indicates that each of the data fields has not been evaluated by rounding professionals 240. Once a checklist field has been evaluated by rounding professionals 240, a mark is placed in check-box 266 to indicate that checklist field 264 has been evaluated. The rounding leading ensures that each of checklist fields 264 is evaluated before concluding IP patient rounds.

EXAMPLE

The following example further describes and demonstrates embodiments within the scope of method 200. The example is given solely for the purpose of illustration and is not to be construed as limiting method 200, as many variations thereof are possible without departing from the spirit and scope of method 200. The example demonstrates the benefits of the disclosed multi-workstation computer display support structure 10 in concert with practice of method 200 in completing IP patient rounds in the ICU.

Rounding tool 204 retrieves from memory stores 208 case-relevant medical data 210 pertaining to an ICU clinical context from a set of case-relevant medical data domains 212. The set of case-relevant medical data domains 212 includes a vitals medical data domain $212_1$, a ventilator medical data domain $212_2$, a laboratory-result medical data domain $212_3$, an imaging medical data domain $212_4$, a nursing medical data domain $212_5$, and a pharmacy medical data domain $212_6$. Vitals medical data domain $212_1$ includes a blood-pressure data field, a heart-rate data field, a body-temperature data field, a respiratory-rate data field, and a pulse-oximetry data field. Each data field of vitals medical data domain $212_1$ includes trended, historical data taken from at least thirty-six hours prior to the initiation of IP patient rounds. Ventilator medical data domain $212_2$ includes a time-of-intubation data field, a mode-of-mechanical-ventilation data field, an initial-ventilator-settings data field, a changes-to-ventilator-settings data field, a duration-of-mechanical-ventilation data field, and a blood-gas data field. Laboratory-result medical data domain $212_3$ includes a pH data field, a K+ data field, a bilirubin data field, a lactate data field, a blood culture data field, a platelets data field, and a PT/INR data field. Imaging medical data domain $212_4$ includes a report data field, an MRI data field, a CT data field, and an ultrasound data field. Nursing medical data domain $212_5$ includes a cognition data field, a daily-activities data field, a caregiver-support data field, a home-environment data field, a health-history data field, a symptom-status data field, a medication-issues data field, a wounds data field, an incisions data field, an emotional status data field, and a pain-scores data field. Pharmacy medical data domain $212_6$ includes a medical history data field, an allergies data field, a contraindications data field, a current-medications data field, a renal-and-hepatic-dosing data field, a patient-specific-factors data field, and a therapeutic-equivalents data field.

Rounding protocols 202 incorporate CDRs relevant to vitals rounding protocol $202_1$, ventilator rounding protocol $202_2$, laboratory-result rounding protocol $202_3$, imaging rounding protocol $202_4$, nursing rounding protocol $202_5$, and pharmacy rounding protocol $202_6$.

Rounding tool 204 generates a set of rounding protocols 202, rounding checklists 220, and rounding cues 222, with each of the set of rounding protocols 202, rounding checklists 220, and rounding cues 222 being set forth in an EHR System-based flowsheet 224. Rounding tool 204 assimilates case-relevant medical data 210 of the set of case-relevant medical data domains 212 into the set of rounding protocols 202; vitals medical data domain $212_1$ is assimilated into a vitals rounding protocol $202_1$; ventilator medical data domain $212_2$ is assimilated into a ventilator rounding protocol $202_2$; laboratory result data domain $212_3$ is assimilated into a laboratory-result rounding protocol $202_3$; imaging medical data domain $212_4$ is assimilated into an imaging rounding protocol $202_4$; nursing medical data domain $212_5$ is assimilated into a nursing rounding protocol $202_5$; and pharmacy medical data domain $212_6$ is assimilated into a pharmacy rounding protocol $202_6$.

A profession-specific presentation schedule includes presentation of rounding protocols $202_1$, $202_2$, $202_3$, $202_4$, $202_5$, and $202_6$, of which rounding protocols $202_1$, $202_2$, $202_3$, and $202_4$ are presented at IP patient rounds by a rounding professional credentialed as a physician, physician's assistant, or nurse practitioner; nursing rounding protocol $202_5$ is presented at IP patient rounds by a rounding professional credentialed as a nurse practitioner, a registered nurse, licensed practical nurse, or clinical nurse specialist; and pharmacy rounding protocol $202_6$ is presented at IP patient rounds by a rounding professional credentialed as a registered pharmacist.

Figure 9:
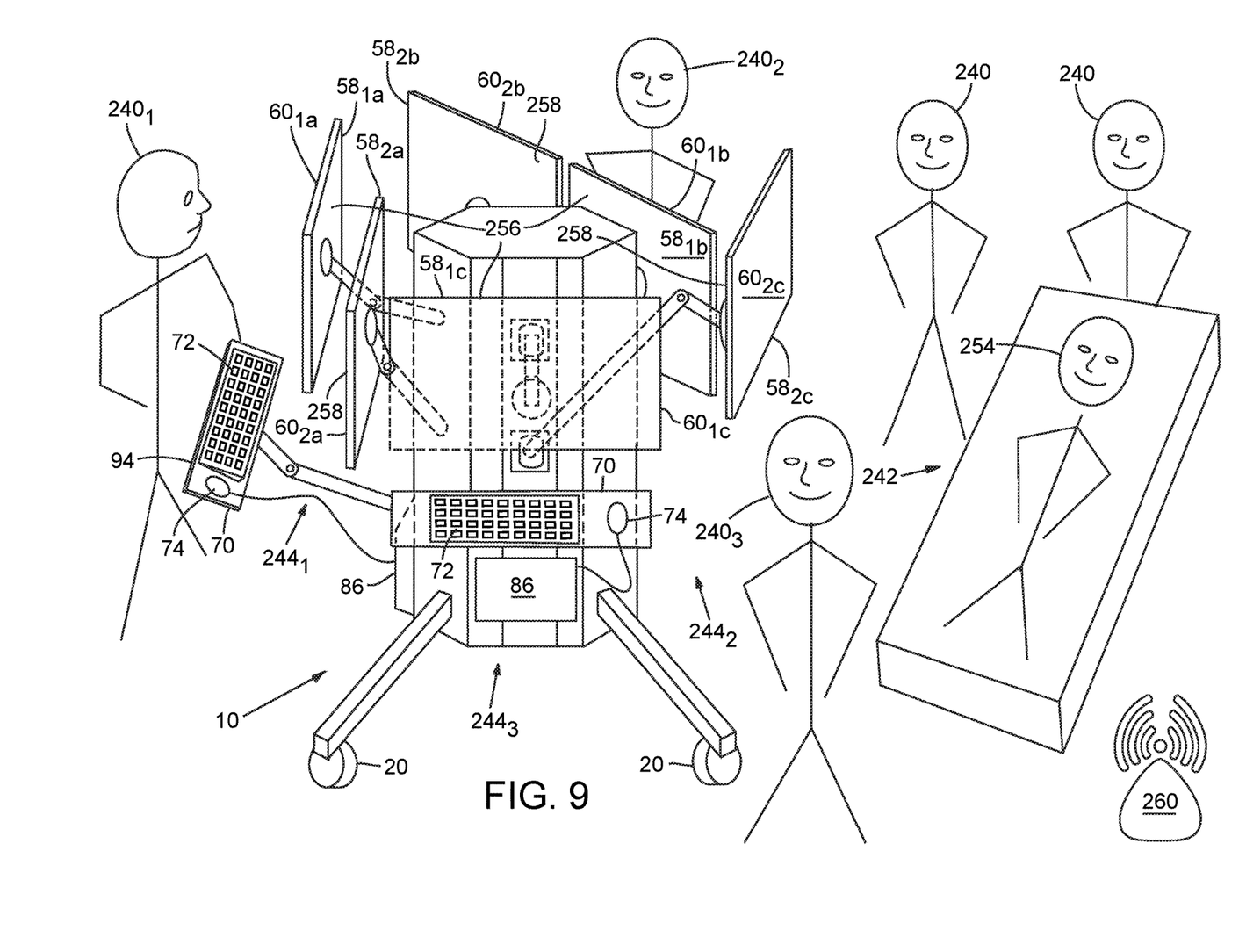
FIG. 9 is a diagram showing several medical professionals participating in IP patient rounds taking place at a patient's bedside, with the computer display support structure of FIG. 1 in use.

FIG. 9 is a diagram showing IP patient rounds taking place with use of computer display support structure 10 at a patient's bedside 242. IP patient rounds in the ICU begin when an inter-profession team of rounding professionals 240 arrives at patient's bedside 242 with a computer display support structure 10 configured to have workstations $244_1$, $244_2$, and $244_3$. Workstation $244_1$ is assigned to a rounding leader $240_1$, who is an attending physician. Workstation $244_2$ is assigned to an order-entry rounding professional $240_2$. Workstation $244_3$ is reserved for a presenting rounding professional $240_3$, who is scheduled to present on the case of a patient 254 according to the profession-specific presentation schedule.

Workstations $244_1$, $244_2$, and $244_3$ each have respective pairs of video displays $58_{1a}/58_{2a}$, $58_{1b}/58_{2b}$, and $58_{1c}/58_{2c}$, a keyboard tray 70; a keyboard 72; and a computer mouse 74. Video displays $58_{1a}$, $58_{1b}$, and $58_{1c}$ of each pair are designated as personalized video displays 256. Video displays $58_{2a}$, $58_{2b}$, and $58_{2c}$ of each pair are designated as shared video displays 258. The EHR System distributes video sources 230 through a wireless network 260 to workstations 244.

Workstations $244_1$, $244_2$, and $244_3$ access video sources $230_1$, $230_2$, and $230_3$ (FIG. 6), respectively, as the video source of personalized video displays 256. Rounding-leader workstation $244_1$ has a video display source controller 94 that selects any one of video sources $230_1$, $230_2$, or $230_3$ as the video source of shared video displays 258 that are simultaneously viewable on video displays $58_{2a}$, $58_{2b}$, and $58_{2c}$.

Order-entry rounding professional $240_2$ takes position at workstation $244_2$ and initiates an order-entry dialog box in the EHR System on workstation $244_2$, using video source $230_2$. The order-entry dialog box (not shown) is an EHR System-based graphical control element that allows an EHR System user to modify the case-relevant medical data. These modifications include the addition of chart notes, requests for new laboratory orders, imaging orders, medication orders, transfer or discharge planning notes, and requests for consultation with medical professionals not part of the inter-professional team.

Rounding leader $240_1$ takes position at workstation $244_1$ and uses video display source controller 94 to select video source $230_3$ as the video source for shared video displays 258 and instructs the scheduled presenting rounding professional $240_3$ to take position at workstation $244_3$. Scheduled presenting rounding professional $240_3$ takes position at workstation $244_3$ and initiates vitals rounding protocol $202_1$ in the EHR System on workstation $244_3$ using video source $230_3$ to display vitals rounding protocol $202_1$.

Video displays 58 are independently positioned by rounding professionals $240_1$, $240_2$, and $240_3$ to locations in space that avoid obstructing eye-contact sightlines $262_1$, $262_2$, and $262_3$. Rounding professionals $240_1$, $240_2$, and $240_3$ periodically make eye contact while facing computer display support structure 10 in order to enhance communication during IP Patient Rounds. Personalized video displays $58_{1a}$, $58_{1b}$, and $58_{1c}$ have display screens $60_{1a}$, $60_{1b}$, and $60_{1c}$, respectively. Display screens $60_{1a}$, $60_{1b}$, and $60_{1c}$ are tilted to generally align with the sightlines of rounding professionals $240_1$, $240_2$, and $240_3$. Shared video displays $58_{2a}$, $58_{2b}$, and $58_{2c}$ have display screens $60_{2a}$, $60_{2b}$, and $60_{2c}$, respectively. Display screens $60_{2a}$, and $60_{2b}$ are selectively tilted to be viewable by rounding professional $240_1$ and rounding professional $240_2$, respectively. Display screen $60_{2c}$, is selectively tilted to be generally viewable by rounding professionals 240 (two shown in FIG. 9) not stationed at workstations 244, patient 254, or any other individual located near patient bedside 242.

Presenting rounding professional $240_3$ verbalizes to the inter-professional team the case-relevant medical data as prompted by rounding protocols 202, beginning with the vitals rounding protocol and then continuing in a consecutive order of the ventilator rounding protocol, the laboratory-result rounding protocol, and the imaging rounding protocol. After the imaging rounding protocol is completed, rounding leader $240_1$ instructs the rounding professional 240 who is assigned to present the nursing rounding protocol to take position at workstation $244_3$ and begin presenting and verbalizing the nursing rounding protocol. After the nursing rounding protocol is completed, rounding leader $240_1$ instructs the rounding professional 240 who is assigned to present the pharmacy rounding protocol to take position at workstation $244_3$ and begin presenting and verbalizing the pharmacy rounding protocol. Rounding leader $240_1$ ensures that the vitals checklist, ventilator checklist, laboratory-result checklist, imaging checklist, nursing checklist, and pharmacy checklist are completed.

If an EHR System-based flowsheet presents a rounding cue, rounding leader $240_1$ instructs the scheduled presenting rounding professional $240_3$ to pause the presentation to allow for the inter-professional team of rounding professionals 240 to investigate and respond. Rounding leader $240_1$ and order-entry rounding professional $240_2$ access the EHR System on workstations $244_1$ and $244_2$, respectively, to investigate or verify case-relevant medical data relevant to the rounding cue. Rounding leader $240_1$ uses video display source controller 94 to select either video source $230_1$ or $230_2$ to display information on shared video displays 258 to show the investigation and response in real-time to rounding professionals 240 not stationed at workstations 244. Rounding leader $240_1$ listens to questions and comments from rounding professionals 240 regarding the investigation, allowing them to offer medical opinion on what clinical decisions should be made.

If the case-relevant medical data need to be modified in order to include additional chart notes, requests for new laboratory orders, imaging orders, medication orders, transfer or discharge planning notes, or requests for consultation with medical professionals not part of the inter-professional team, the orders or modifications will be made by order-entry rounding professional $240_2$. Rounding leader $240_1$ will use video display source controller 94 to select video source $230_2$ as the video source to display information on shared video displays 258 to allow rounding professionals 240 to simultaneously review the modifications to the case-relevant medical data in real-time.

After the vitals rounding protocol, ventilator rounding protocol, laboratory-result rounding protocol, and imaging rounding protocol, nursing rounding protocol, and pharmacy rounding protocol are complete, rounding leader $240_1$ uses video display source controller 94 to select video source $230_2$ as the video source to display information on shared video displays 258 and instructs the order-entry rounding professional $240_2$ to complete an order-readback step. An order-readback step includes a verbalization by the order-entry rounding professional $240_2$ to the rounding professionals 240 of new chart notes, laboratory orders, imaging orders, medication orders, transfer or discharge planning notes, or requests for consultation with medical professionals not part of the inter-professional team. Rounding professionals 240 simultaneously review the order-readback step graphically on shared displays 258 in real-time.

Once rounding professionals 240 have completed rounding protocols 202, modifications to the case-relevant medical data 210, and an order-readback step, all modifications and orders will be signed by rounding leader $240_1$.

It will be obvious to those having skill in the art that many changes may be made to the details of the above-described embodiments without departing from the underlying principles of the invention. The scope of the present invention should, therefore, be determined only by the following claims.

The invention claimed is:

1. A computer display support structure for reducing EHR-related medical errors during IP patient rounds, comprising:

an upright column assembly having a column assembly base, the upright column assembly defining a longitudinal axis and having an exterior surface and a periphery;

multiple mounting brackets positioned at different, peripherally spaced-apart locations on the exterior surface and around the periphery of the upright column assembly, the peripherally spaced-apart locations spaced apart from each other around the upright column in a direction that is at least substantially perpendicular to the longitudinal axis to define multiple different workstations around the periphery of the upright column assembly;

multiple system device mounting assemblies configured for attachment to the multiple mounting brackets so that at least two of the multiple system device mounting assemblies, when attached to an associated one of the multiple mounting brackets, are positioned at each one of the multiple different workstations and the at least two of the multiple system device mounting assemblies at each one of the multiple different workstations is spaced apart from each other in a direction generally along the longitudinal axis of the upright column assembly and configured for pivotal movement independent of each other;

a video display mounted to at least one of the at least two system device mounting assemblies at each of the multiple different workstations and having a display screen providing for an observer a viewing angle that is adjustable in correspondence with the pivotal movement; and a video display source controller capable of responding to a user-provided command to select a source of video for delivery to one or more of the video displays.

2. The computer display support structure of claim 1, in which a plurality of the system device mounting assemblies are constructed for selective extension to different distances laterally from the longitudinal axis of the upright column assembly.

3. The computer display support structure of claim 1, in which the upright column assembly is tubular.

4. The computer display support structure of claim 1, in which:
- the upright column assembly is formed of multiple sides defining a polygonal exterior surface; and
- the multiple mounting brackets are positioned at different non-contiguous ones of the multiple sides of the upright column assembly.

5. The computer display support structure of claim 1, in which each one of a set of the multiple system device mounting assemblies includes a system device arm that, at a proximal end, is pivotally connected to a pivot arm for pivotal movement about a first axis generally parallel to the longitudinal axis and a second axis transverse to the first axis and, at a distal end, is pivotally connected to a coupling member, the coupling member configured for pivotal connection to a system device.

6. The computer display support structure of claim 5, in which one of the multiple system device mounting assemblies is configured to support a keyboard.

7. The computer display support structure of claim 1, further comprising:
- a CPU platform attached to one of the multiple mounting brackets;
- a CPU attached to the CPU mounting platform; and
- a CPU power supply attached to the column assembly base of the upright column assembly.

8. The computer display support structure of claim 1, in which a set of support legs is attached to the column assembly base, each support leg of the set extending radially outwardly from the upright column assembly.

* * * * *